US00PP33580P2

(12) United States Plant Patent
Gitzels et al.

(10) Patent No.: US PP33,580 P2
(45) Date of Patent: Oct. 26, 2021

(54) ***DAHLIA* PLANT NAMED 'BALDADENYEL'**

(50) Latin Name: *Dahlia variabilis*
Varietal Denomination: Baldadenyel

(71) Applicant: Ball Horticultural Company, West Chicago, IL (US)

(72) Inventors: Jeroen Gitzels, Zwaag (NL); Valentin Taquet, Amsterdam (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/334,214

(22) Filed: May 28, 2021

Related U.S. Application Data

(60) Provisional application No. 63/140,305, filed on Jan. 22, 2021.

(51) Int. Cl.
*A01H 6/14* (2018.01)
*A01H 5/02* (2018.01)

(52) U.S. Cl.
USPC ..... Plt./321

(58) Field of Classification Search
USPC ..... Plt./321
See application file for complete search history.

*Primary Examiner* — Annette H Para

(74) *Attorney, Agent, or Firm* — Audrey Charles

(57) ABSTRACT

A new and distinct cultivar of *Dahlia* plant named 'Baldadenyel', characterized by its double-type, medium yellow colored inflorescences, dark green-colored foliage, and vigorous, upright-mounded growth habit, is disclosed.

1 Drawing Sheet

Latin name of genus and species of plant claimed: *Dahlia variabilis*.

Variety denomination: 'Baldadenyel'.

BACKGROUND OF THE INVENTION

The present invention relates to a new and distinct cultivar of *Dahlia* plant botanically known as *Dahlia variabilis* and hereinafter referred to by the cultivar name 'Baldadenyel'.

The new cultivar originated in a controlled breeding program in Hem, The Netherlands during August 2015. The objective of the breeding program was the development of *Dahlia* cultivars that are freely flowering with large inflorescences, mid-season flower timing, and a vigorous, upright-mounded growth habit.

The new *Dahlia* cultivar is the result of open pollination. The female (seed) parent of the new cultivar is the proprietary *Dahlia variabilis* breeding selection coded D16-226-1, not patented, characterized by its double type, light yellow-colored inflorescences, medium green-colored foliage, and moderately vigorous, upright-mounded growth habit. The male (pollen) parent of the new cultivar is unknown. The new cultivar was discovered as a single flowering plant within the progeny of the above stated open pollination during July 2016 in a controlled environment in Hem, The Netherlands.

Asexual reproduction of the new cultivar by terminal stem cuttings since July 2016 in Hem, The Netherlands and Andijk, The Netherlands has demonstrated that the new cultivar reproduces true-to-type with all the characteristics, as herein described, firmly fixed and retained through successive generations of such asexual propagation.

SUMMARY OF THE INVENTION

The following characteristics of the new cultivar have been repeatedly observed and can be used to distinguish 'Baldadenyel' as a new and distinct cultivar of *Dahlia* plant:

1. Double-type, medium yellow colored inflorescences;
2. Dark green-colored foliage; and
3. Vigorous, upright-mounded growth habit.

Plants of the new cultivar differ from plants of the female parent primarily in having darker yellow colored inflorescences.

Of the many commercially available *Dahlia* cultivars, the most similar in comparison to the new cultivar is HYPNOTICA Yellow 'Dodahhypnoyel 19', U.S. Plant Pat. No. 31,761. However, in comparison, plants of the new cultivar differ from plants of 'Dodahhypnoyel 19' in at least the following characteristics:

1. Plants of the new cultivar have slightly darker yellow colored inflorescences than plants of 'Dodahhypnoyel 19';
2. Plants of the new cultivar have larger diameter inflorescences than plants of 'Dodahhypnoyel 19'; and
3. Plants of the new cultivar have higher growth vigor than plants of 'Dodahhypnoyel 19'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldadenyel'. The 14-week-old plants were grown in 6.5-inch pots for 10 weeks in a glass-covered greenhouse in Hem, The Netherlands. Plants were given one pinch before transplant.

DETAILED BOTANICAL DESCRIPTION

Figure 1:
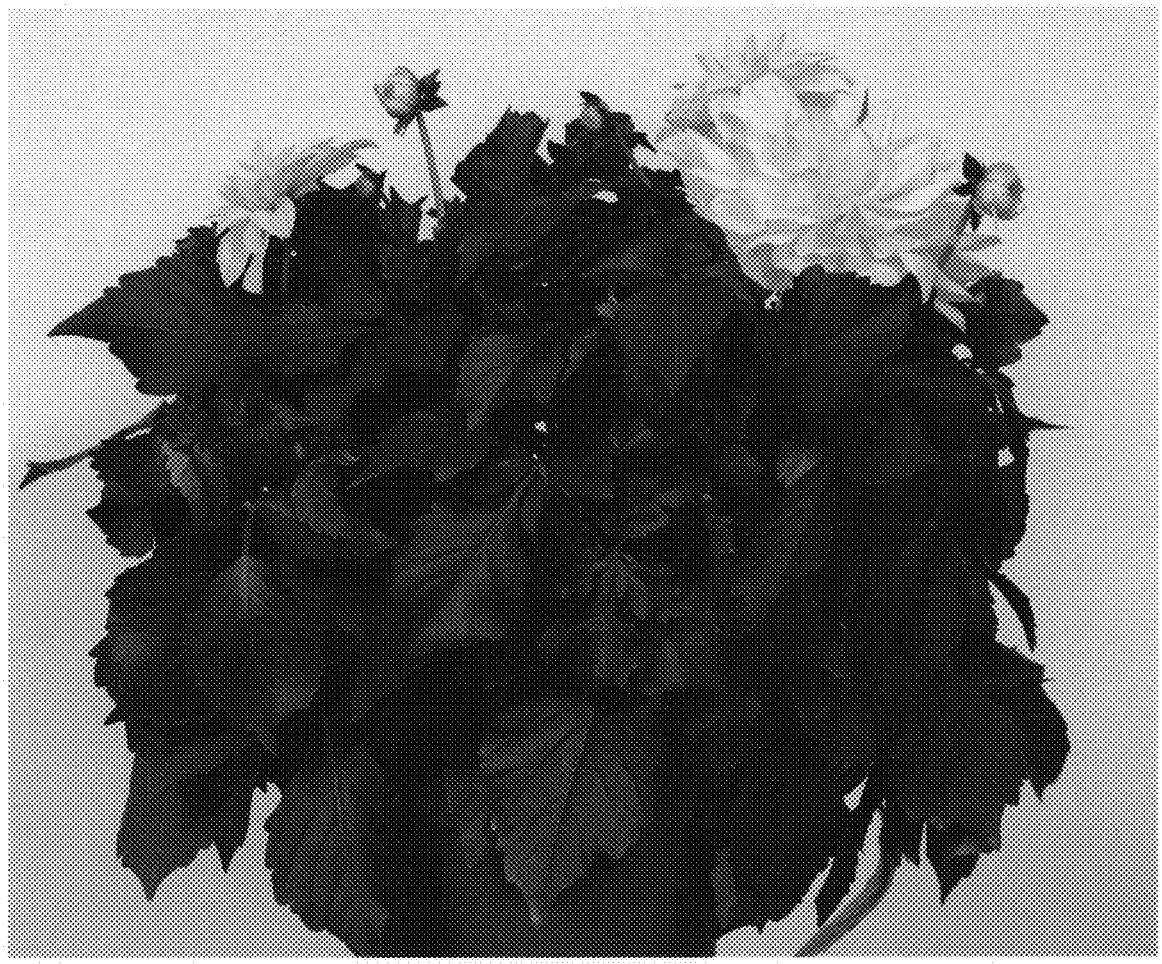
FIG. 1 illustrates a side view of the overall growth and flowering habit of 'Baldadenyel'.
Figure 2:
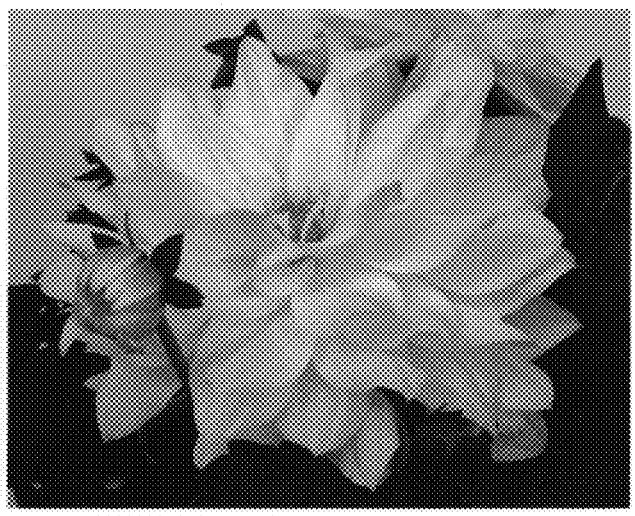
FIG. 2 illustrates a close-up view of an individual inflorescence of 'Baldadenyel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in March 2021 under natural light conditions in Boskoop, The Netherlands.

The following descriptions and measurements describe 14-week-old plants produced from cuttings from stock plants and grown in a glass-covered greenhouse under conditions comparable to those used in commercial practice. The plants were grown in Hem, The Netherlands in 6.5-inch pots for 10 weeks utilizing a soilless growth medium. Plants were given one pinch before transplant. Three Daminozide treatments were applied: one at 2,500 ppm two weeks after transplant, a second at 3,000 ppm four weeks after transplant and a third at 3,500 ppm six weeks after transplant. Greenhouse temperatures were maintained at an average of approximately 64° F. (18° C.) during the day and approximately 61° F. (16° C.) during the night. Supplemental lighting was used. Measurements and numerical values represent averages of typical plants. #

Botanical classification: *Dahlia variabilis* 'Baldadenyel'.

Parentage:

*Female parent.*—Proprietary *Dahlia variabilis* breeding selection coded D16-226-1, not patented.

*Male parent.*—Unknown.

Propagation:

*Type cutting.*—Terminal stem.

*Time to initiate roots.*—Approximately 9 to 12 days.

*Time to produce a rooted cutting.*—Approximately 25 to 32 days.

*Root description.*—Fine, fibrous.

*Rooting habit.*—Freely branching.

Plant description:

*Commercial crop time.*—Approximately 7 to 9 weeks from a rooted cutting to finish in a 15 cm pot.

*Growth habit and general appearance.*—Vigorous, upright-mounded.

*Size.*—Height from soil level to top of plant plane: Approximately 30.2 cm. Height from soil level to top of foliage: Approximately 28.0 cm. Width: Approximately 46.8 cm.

*Branch.*—Quantity of lateral branches per plant: Approximately 7. Strength: Moderately strong. Length of lateral branch: Approximately 21.1 cm. Diameter of lateral branch at central internode: Approximately 7.0 mm. Length of central internode of lateral branch: Approximately 2.9 cm. Texture: Glabrous. Color: 146B with 144A.

Foliage description:

*General description.*—Quantity of leaves per lateral branch: Approximately 16. Type: Compound. Quantity of leaflets per compound leaf: Approximately 3 or 5. Fragrance: None detected. Arrangement: Opposite. Aspect: Petiole mostly perpendicular angle to stem with blade extending downward. Shape of leaflet: Ovate to broadly elliptic. Margin of leaflet: Widely serrate. Apex of leaflet: Acute. Base of leaflet: Broadly attenuate. Venation pattern: Pinnate.

*Mature compound leaf.*—Shape: Broadly ovate in outline. Length of mature compound leaf: Approximately 14.5 cm to 15.9 cm. Width of mature compound leaf: Approximately 16.2 cm to 18.1 cm. Length of terminal leaflet: Approximately 9.8 cm. Width of terminal leaflet: Approximately 5.8 cm to 7.0 cm. Length of lateral leaflet: Approximately 8.2 cm. Width of lateral leaflet: Approximately 5.2 cm. Texture of upper and lower surfaces: Sparsely pubescent. Color of upper surface: 147A blended with N189A. Color of lower surface: 191A. Length of petiole of mature compound leaf: Approximately 4.0 cm to 4.8 cm. Diameter of petiole of mature compound leaf: Approximately 4.0 mm. Texture of upper and lower surfaces of petiole: Glabrous. Color of upper surface of petiole: 144A with 143A. Color of lower surface of petiole: 144A. Length of rachis: Approximately 2.6 cm. Diameter of rachis: Approximately 2.0 mm to 4.3 mm. Texture of upper and lower surfaces of rachis: Glabrous. Color of upper and lower surfaces of rachis: 144A.

Flowering description:

*Flowering habit.*—'Baldadenyel' is freely flowering under outdoor growing conditions with substantially continuous blooming from summer through autumn.

*Lastingness of individual inflorescence on the plant.*—Approximately 2 weeks.

Inflorescence description:

*General description.*—Type: Double, composite, consisting of multiple rows or ray florets, and disc florets, persistent. Aspect: Facing upward and outward. Arrangement: Terminal, arising from leaf axils on strong peduncles positioned over the foliage. Disc and ray florets arranged acropetally on a capitulum. Quantity per plant: Approximately 2. Fragrance: None. Shape: Hemispherical when ray florets are fully open. Inflorescence diameter: Approximately 14.3 cm. Inflorescence depth: Approximately 8.9 cm. Disc diameter: Approximately 2.0 cm. Receptacle diameter at base: Approximately 8.0 mm. Receptacle depth: Approximately 4.0 mm. Receptacle color: 145C.

*Peduncle.*—Strength: Strong. Aspect: Erect. Length: Approximately 14.8 cm. Diameter: Approximately 4.5 mm. Texture: Glabrous. Color: 144A.

*Bud.*—Rate of bud opening: Generally takes 2 weeks for bud to progress from first color to fully open flower. Quantity per plant: Approximately 18.

*Bud just before opening.*—Shape: Oblate. Depth at first color: Approximately 1.5 cm. Diameter at first color: Approximately 1.9 cm. Texture: Glabrous. Color: Outer surface of the phyllaries N154A with base of 143B, and immature ray florets of 2A.

*Ray florets.*—Quantity per inflorescence: Approximately 80. Arrangement: Imbricate, in multiple whorls. Aspect: Flat to very slightly convex and slightly twisted. Shape: Oblanceolate. Margin: Entire. Apex: Apiculate. Base: Attenuate. Appearance: Matte. Length: Approximately 6.7 cm. Width: Approximately 2.7 cm. Texture of upper surface: Glabrous. Texture of lower surface: Glabrous, ribbed. Color of upper surface when first and fully open: 4A to 4B with base of 6B. Color of lower surface when first and fully open: 1A with base of 6B. Color of upper surface before senescence: 1A to 1B. Color of lower surface before senescence: 1B.

*Disc florets.*—Quantity per inflorescence: Approximately 50. Arrangement: Massed in center of inflorescence. Aspect: Erect. Shape: Tubular. Margin: Entire. Apex: 5 acute tips. Base: Fused. Length: Approximately 1.7 cm. Diameter at apex: Approximately 5.0 mm. Diameter at base: Approximately 1.0 mm. Texture: Glabrous. Color when fully open: 14A with midsection of 13A and 157D at base, translucent.

*Outer phyllaries.*—Quantity: Approximately 6 to 8. Aspect: Flat, slightly reflexed. Shape: Narrowly elliptic. Margin: Entire. Apex: Acute. Base: Truncate. Length: Approximately 2.0 cm. Width: Approximately 9.0 mm. Texture of upper and lower surfaces: Glabrous. Color of upper surface: 137A. Color of lower surface: 138A.

*Inner phyllaries.*—Quantity: Approximately 1 per floret. Shape: Linear, imbricate. Margin: Entire. Apex: Broadly acute to obtuse. Base: Truncate. Length of outermost: Approximately 2.2 cm. Width of outermost: Approximately 6.0 mm. Length of innermost: Approximately 1.4 cm. Width of innermost: Approximately 5.0 mm. Texture of upper and lower surfaces: Glabrous. Color of upper and lower surfaces: 151B to 151C, translucent with 143A at base of outermost.

*Reproductive organs.*—Androecium: On disc florets. Stamen quantity: 5 per floret. Stamen length: Approximately 1.0 cm. Anther shape: Linear. Anther length: Approximately 5.0 mm. Anther color: 153C. Pollen amount: Moderate. Pollen color: 17A. Gynoecium: On disc florets. Pistil length: Approximately 1.3 cm. Stigma shape: 2 branched. Stigma length: Approximately 3.0 mm. Stigma width: Approximately 4.0 mm. Stigma color: 14A to 14B. Style length: Approximately 1.0 cm. Style color: 154B. Ovary length: Approximately 2.0 mm. Ovary color: 145C.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldadenyel', substantially as herein illustrated and described.

* * * * *